United States Patent [19]

Norden

[11] Patent Number: 5,114,976
[45] Date of Patent: May 19, 1992

[54] METHOD FOR TREATING CERTAIN PSYCHIATRIC DISORDERS AND CERTAIN PSYCHIATRIC SYMPTOMS

[76] Inventor: Michael J. Norden, 348 NW. 113th Pl., Seattle, Wash. 98177

[21] Appl. No.: 610,339

[22] Filed: Nov. 5, 1990

Related U.S. Application Data

[63] Continuation of Ser. No. 294,461, Jan. 6, 1989, abandoned.

[51] Int. Cl.⁵ ............................................. A61K 31/135
[52] U.S. Cl. ........................................................ 514/646
[58] Field of Search ........................................... 514/646

[56] References Cited

U.S. PATENT DOCUMENTS 4,314,081  2/1982  Molloy et al. ................... 564/347
4,626,549  12/1986  Molloy et al. .................... 514/651
4,647,591  3/1987  Cherkin et al. .................... 514/651

OTHER PUBLICATIONS

Chem. Abst. 106-43304b (1987).

Primary Examiner—S. J. Friedman
Attorney, Agent, or Firm—Seed and Berry

[57] ABSTRACT

There is disclosed a method for treating psychiatric disorders including circadian rhythm disorders, borderline personality disorders, personality disorders, Late Luteal Phase Dysphoric Disorder, psychoactive substance use disorders, sexual disorders, and schizophrenia and certain psychiatric symptoms including stress, anger, worry, rejection sensitivity and lack of mental or physical energy with administration of a nontoxic dose of a serotonin re-uptake blocker. Preferably, the serotonin re-uptake blocker is fluoxetine or norfluoxetine.

3 Claims, No Drawings

METHOD FOR TREATING CERTAIN PSYCHIATRIC DISORDERS AND CERTAIN PSYCHIATRIC SYMPTOMS

CROSS-REFERENCE TO RELATED APPLICATION

This application is a continuation of U.S. application Ser. No. 07/294,461 filed Jan. 6, 1989, now abandoned.

TECHNICAL FIELD

The present invention relates to a method of treating various psychiatric disorders and psychiatric symptoms with a class of pharmaceutical compounds called serotonin re-uptake blocking agents.

BACKGROUND OF THE INVENTION

The present invention relates to the treatment of six different types of psychiatric disorders and treatment of several specific symptoms. The disorders and their clinical manifestations are known to practicing psychiatrists, but are briefly described herein from the American Psychiatric Association, *The Diagnostic and Statistical Manual of Mental Disorders*. The specific symptoms can be recognized by most psychiatrists.

Personality traits are enduring patterns of perceiving, relating to, or thinking about the environment and ones self, and are exhibited in wide range of important social and personal contexts. It is only when personality traits are inflexible and maladaptive and cause either significant functional impairment or subject distress that they constitute personality disorders. The manifestations of personality disorders are often recognizable by adolescence or earlier and continue throughout most of adult life. The diagnostic criteria for the personality disorders refer to behaviors or traits that are characteristic of the person's recent and long-term functioning since early adulthood. The constellation of behaviors or traits causes either significant impairment in social or occupational functioning or subjective distress.

Personality disorders are notoriously difficult to reliably distinguish from one another. The validity of the distinctions is often called into question, as for example on many psychological variables testing cannot distinguish borderline personality disorder (BPD) from antisocial personality disorder. Personality disorders and BPD are closely linked, and most commonly women will receive the diagnosis of BPD and men antisocial personality disorder (APD).

The vast majority of people in prison have antisocial personality disorder or many traits of the syndrome. This is generally regarded as unresponsive to treatment. There is an apparent need for more effective treatment which would be of benefit both to these individuals and society as a whole.

Borderline personality disorder (BPD) comprise a pervasive pattern of instability of self-image, interpersonal relationships and mood, beginning by early adulthood and present in a variety of contexts.

BPD is characterized by a marked and persistent identity disturbance. The identity disturbance is often pervasive, and is manifested by uncertainty about several life issues, such as self-image, sexual orientation, long-term goals or career choice, types of friends or lovers to have, or which values to adopt. The BPD person often experiences this instability of self-image as chronic feelings of emptiness or boredom. Interpersonal relationships are usually unstable and intense, and may be characterized by alternation of the extremes of over-idealization and devaluation. These people have difficulty tolerating being alone, and will make frantic efforts to avoid real or imagined abandonment.

*The Diagnostic and Statistical Manual of Mental Disorders* (DSM-III-R) of the American Psychiatric Association characterizes BPD as indicated by at least five of the following eight symptoms.

1. A pattern of unstable and intense interpersonal relationships characterized by alternating between extremes of over-idealization and devaluation.

2. Impulsiveness in at least two areas that are potentially self-damaging, e.g., spending, sex, substance use, shoplifting, reckless driving, or binge eating.

3. Affective instability: marked shifts from baseline mood to depression, irritability, or anxiety, usually lasting a few hours and only rarely more than a few days.

4. Inappropriate, intense anger or lack of control of anger, e.g., frequent displays of temper, constant anger or recurrent physical fights.

5. Recurrent suicidal threats, gestures, or behavior or self-mutilating behavior.

6. Marked and persistent identity disturbance manifested by uncertainty about at least two of the following:
   self-image, sexual orientation, long-term goals or career choice, type of friends desired or preferred values.

7. Chronic feelings of emptiness or boredom.

8. Frantic efforts to avoid real or imagined abandonment.

Patients with BPD are among the most challenging and treatment-resistant patients seen in psychotherapy. BPD patients account for 15% to 25% of patients in both inpatient and outpatient mental health settings (Gunderson et al., "Current Overview of the Borderline Diagnosis," *J. Clin. Psychiatry* 49:5-14, 1987). BPD patients carry a 10% risk of completed suicide over a 10 to 15 year follow-up (Stone, "Psychotherapy of Borderline Patients in Light of Long-Term Follow-Up," *Bull. Menninger Clin.* 51:231-247, 1987). Many practitioners turn to pharmacotherapy in the management of this disorder, but there are very few studies to guide treatment. Cowdry et al. "Pharmacology of Borderline Personality Disorder," *Arch. Gen. Psychiatry* 45:111-119, 1988, discloses that medications, principally monoamine oxidase inhibitors, carbamazepine and neuroleptics are useful but are generally of "limited benefit." Therefore, there is a compelling need for safer, more effective, and better-tolerated treatment of BPD.

BPD is more commonly diagnosed in females and is apparently a common disorder.

Late Luteal Phase Dysphoric Disorder (LLPDD) is the current term associated with Premenstrual Syndrome (PMS). Many females report a variety of physical and emotional changes associated with specific phases of the menstrual cycle. For most of these females, these changes are not severe, cause little distress, and have no effect on social or occupational functioning. In contrast, the essential feature of LLPDD is a pattern of clinically significant emotional and behavioral symptoms that occur during the last week of the luteal phase and remit within a few days after the onset of the follicular phase. In most females, these symptoms occur in the week before and remit within a few days after the onset of menses.

LLPDD is diagnosed only if the symptoms are sufficiently severe to cause marked impairment in social or occupational functioning and have occurred during a majority of menstrual cycles in the past year.

Among the most commonly experienced symptoms are marked affective lability (e.g., sudden episodes of tearfulness, sadness, or irritability); persistent feelings of irritability, anger or tension (feeling "on edge"); and feelings of depression and self-deprecating thoughts. Also common are decreased interest in usual activities, fatigability and loss of energy, a subjective sense of difficulty in concentrating, changes in appetite, cravings for specific foods (especially carbohydrates), and sleep disturbance. Other physical symptoms, such as breast tenderness or swelling, headaches, joint or muscle pain, a sensation of "bloating," and weight gain, may also be present.

Generally non-steroidal anti-inflammatory drugs are administered to LLPDD patients, but these are only effective for some of the physical symptoms. "The complaints of PMS, if severe, may be treated symptomatically. Water retention may be relieved by diet or antidiuretic medication. Severity of water retention does not always correlate with psychological symptoms. Preliminary recent studies have suggested that spironolacture (Aldactone, Searle) may also be effective in relieving depression and crying spells.

Other drugs, including progesterone, lithium carbonate, thiazide, diuretics, antidepressants and bromocyptone (Parlodel, Sandoz), have been tried with uncertain success." *Comprehensive Textbook of Psychiatry IV.*

Circadian rhythm disorders are characterized by insufficient and/or unsatisfying sleep, often associated with certain types of professional activities (for example, shift-workers and travel schedules of airline personnel and air travelers). The circadian system has a key role in the regulation of the disorder of the circadian sleep-wake rhythm. It has been estimated that between 5 and 20% of the adult population in western countries suffer from insufficient and/or unsatisfying sleep.

The DSM III-R has characterized circadian rhythm disorders as "sleep-wake" schedule disorders. The essential feature of the sleep-wake schedule disorder is a mismatch between the normal sleep-wake schedule that is demanded by the person's environment and the person's circadian rhythm. This results in a complaint of either insomnia (the person attempts to sleep but is unable to do so) or hypersomnia (the person is unable to remain alert when wakefulness is expected). Transient sleep-wake schedule mismatches commonly occur when people change time zones rapidly or occasionally stay up late for several days. The frequently changing type of sleep-wake schedule disorder is apparently due to frequent changes in sleep and waking times. This is often associated with frequent airplane flights involving time-zone changes or with changing work schedules (shift work). Sleep is then often divided into two periods (e.g., napping both before and after work). On weekends or on days off, the person may temporarily attempt to revert to a normal sleep-wake schedule and thus undermine a long-term circadian adaptation to the new work schedule. For reasons as yet unknown, people vary greatly in their ability to tolerate frequently changing sleep-wake schedules. Some people work for years on rotating work shifts without experiencing any distress. In general, older people have more difficulty adjusting to frequent schedule changes.

The benzodiazepines are the present treatment of choice for the management of circadian rhythm disorders. Benzodiazepines are thought to act by potentiating the action of the neurotransmitter gammaaminobutyric acid (GABA), a widely distributed transmitter in the central nervous system. Turek et al. ("A Benzodiazepine Used in the Treatment of Insomnia Phase-Shifts the Mammalian Circadian Clock," *Nature* 321:167–168, 1986) reports that the acute administration of triazolam, a short-acting benzodiazepine commonly prescribed for the treatment of insomnia, induces a phase-shift in the circadian rhythm of locomotor activity in golden hamsters. Turek et al. suggests a role for GABA-containing neurons in the mammalian circadian system. Turek et al. does not disclose or suggest a serotonin effect for the circadian system.

Short-acting triazolobenzodiazepines, such as triazolam are associated with anterograde amnesia and more pronounced withdrawal effects which aggravate addiction potential. Accordingly, it is addiction potential and other side effects that creates a need for better tolerated and more effect in treatments for circadian rhythm disorders.

Moreover, Wright et al., "The Effects of Exogenous Melatonin on Endocrine Function in Man," *Clin. Endocrinol.* 24:375–382 (1986), suggest the therapeutic use of melatonin for the treatment of jet lag as not having other complications from other undesirable endocrine effects. However, in an editorial (Lancet, Aug. 30, 1986, p. 493) concluded that the efficacy and safety data for melatonin did not justify its use for jet lag. Therefore, there is a need in the art for an effective and relatively nontoxic medication to help the frequently changing type of sleep-wake schedule disorder individuals cope with time-zone changes or with changing work schedules.

Psychoactive substance abuse and dependence is characterized by a cluster of cognitive, behavioral, and physiologic symptoms that indicate that the person has impaired control of his psychoactive substance use and continues use of the substance despite adverse consequence. The American Handbook of Psychiatry (Vol 8. "Biologic", 2nd ed p. 87), states:

Sadly, long-term treatment and rehabilitation programs for patients with substance abuse disorders are far less successful than treatment of their acute reactions. Most substance abusers revert rapidly to the dangerous patterns of drug self administration that initially caused the acute toxic reactions . . . . Medical research is urgently needed to develop new treatment approaches for the chronic maladaptive and self-destructive behaviors of substance abusers."

The cost of the drug problem in the U.S. alone is estimated at 100 billion dollars.

Schizophrenia is characterized by the presence of characteristic psychotic symptoms during the active phase of the illness, and functioning below the highest level previously achieved. At some phase of the illness, schizophrenia always involves delusions, hallucinations, or certain characteristic disturbances in affect and the form of thought. The active phase of schizophrenia is characterized by the presence of at least delusions, prominent hallucinations, incoherence or marked loosening of associations, catatonic behavior, flat or grossly inappropriate affect, bizarre delusions (such as being controlled by a dead person), or prominent hallucinations.

Schizophrenia is a prevalent psychiatric disorder. The importance of schizophrenia as a prevalent problem and the inadequacy of current treatment is evidenced in Kapln et al "The Comprehensive Textbook of Psychiatry". Williams Wilkens. Baltimore. Fourth Edition (1985) page 650 which states "An estimated two million Americans suffer from schizophrenia today. Approximately half of these individuals will experience a course of illness requiring continuous or intermittent dependence upon others for their support. with particular reliance on public support mechanisms." Accordingly. more effective treatment for schizophrenia is needed.

The sexual disorders of the present invention are divided into paraphilias and sexual dysfunctions. including premature ejaculation. Paraphilias are recurrent intense sexual urges and sexually arousing fantasies generally involving either (1) nonhuman objects. (2) the suffering or humiliation of oneself or one's partner (not merely simulated). or (3) children or other nonconsenting persons. The paraphilia patient has either acted on these urges or is markedly distressed by them.

Current treatment for hypersexual states is generally with antitestosterone agents. In the U.S. only Methoxyprogesetrone is used. The efficacy and morality of this treatment is controversial. especially in light of the risks of steroid use.

Other sexual disorders include premature ejaculation. No current pharmacologic therapy is available for premature ejaculation. This is important because many individuals are reluctant or unable to engage in sex therapy with a psychotherapist or lack for a cooperative partner for assisting with behavioral treatment.

Many disorders in psychiatry are actually single symptoms that are sometimes diagnosed as certain disorders if put into symptom clusters. However physicians who do not specialize in psychiatry often will treat symptoms without making a disorder diagnosis. Physicians often lack the therapeutic agents that are directed to specific symptoms rather than a specific psychiatric diagnosis. The symptoms investigated herein include stress, worry, anger, rejection sensitivity and lack of mental or physical energy.

Stress related illnesses are estimated to cause 150 billion dollars per year in treatment associated costs (Koppel Report. ABC NEWS. Dec. 26. 1988). These illnesses include heart attacks. "strokes". ulcers and other stress related illnesses.

Anger is now considered the main toxic element of the "Type A" personality which is considered to be at elevated risk for heart disease. Anger is also a central factor in domestic violence and violence in general.

Rejection sensitivity is among the most obvious symptom of many personality disorders. The patient becomes extremely upset, angry or depressed in response to what they interpret (frequently incorrectly) as rejection, abandonment, or criticism. One variation of this symptom has been termed rejection-sensitive dysphoria and is thought to be responsive only to monoamine oxidase inhibitors and not to other antidepressants. The toxicity and risks of this class of antidepressants, especially the hypertensive or "cheese reaction," limit their use. Accordingly, a drug with a low toxicity profile would be extremely useful for rejection sensitivity.

The symptoms of low mental or physical energy is often addressed with the use of stimulants. Currently available stimulants which are most effective are also most addicting. Illicit use of dextroamphetamine is common among truck drivers who need to maintain alertness over long periods. However dextroamphetmine tends to be dangerous in terms of driver safety (i.e.. amphetamine psychosis or rebound acute drowsiness). as well as being addicting.

Millions of Americans each year receive psychotherapy. There has long been interest in facilitating the often slow and unproductive process of psychotherapy by the use of psychotropics. This may date back to Freud and his experimentation with cocaine. More recent attempts have encountered similar difficulties. Initial enthusiasm for results was tempered by the realization of the toxicity or addiction risk of the agent. Examples include LSD in the 1960's and in the past decade ecstacy (MDMA). Currently. no available agent is established as both safe and effective in facilitating psychotherapy.

Any form of psychotherapy must address the patient's "resistance" to change. The patient is generally not conscious of this resistance. The resistance may arise from denial of a problem because acknowledging the problem may seem overwhelmingly stressful to the patient. It may stem from a patient's inability to disengage from a particular worry. and look with a less rigid mindset at a larger picture.

In patient's with personality disorders. rejection sensitivity may disrupt the alliance with the therapist as offense is taken to words or actions perceived by the patient as critical. rejecting. or lacking empathy. This same sensitivity. coupled with a tendency to react in anger. tends to lead to a series of crisises in the patient's life which can occupy a majority of therapy sessions. thereby precluding focus on important underlying problems. At times. inertia itself may be the biggest barrier as a patient may lack the very mental energy required to do the difficult work of making changes in long entrenched patterns of thinking and behavior.

Accordingly. there are a variety of psychiatric disorders and symptoms that do not have an acceptable therapeutic index in terms of usefulness and lack of toxicity. This invention was made to fulfill a therapeutic need in the specific disorders and symptoms listed.

SUMMARY OF THE INVENTION

The present invention relates to a method for treatment of circadian rhythm disorders, personality disorders (including borderline and antisocial personality disorders personality disorders), hypochondriasis, late luteal phase dysphoric disorder, psychoactive substance use disorders (except for nicotine and alcohol), sexual disorders, and schizophrenia, and related symptoms including stress, worry, anger, rejection sensitivity and lack of mental or physical energy. The present invention also relates to a method for enhancing psychotherapy.

The treatment involves a nontoxic dose of a serotonin re-uptake blocker. Preferred and known serotonin re-uptake blockers include fluoxetine, clomipramine, zimelidine, fluvoxamine, sertraline, indalpine, citalopram, femoxetine, paroxetine, alaproclate, and gepirone. The serotonin re-uptake blockers also include derivatives and pharmaceutically acceptable salts thereof. For example, an active serotonin re-uptake blocker derivative of fluoxetine is norfluoxetine. Preferably, the serotonin re-uptake blocker is fluoxetine or norfluoxetine.

Non-toxic daily doses are indicated. The preferred daily adult dose of fluoxetine or norfluoxetine is from about 1 mg to about 80 mg.

DETAILED DESCRIPTION OF THE INVENTION

I have discovered that the administration of a serotonin re-uptake blocker to human patients suffering from the following psychiatric disorders (circadian rhythm disorders, personality disorders including borderline personality disorder, hypochondriasis, late luteal phase dysphoric disorder, psychoactive substance use disorders, sexual disorders and schizophrenia) and the following psychiatric symptoms (stress, anger, rejection sensitivity, worry and lack of mental or physical energy) is useful in the effective management and treatment of the specific disorders or specific symptoms. This result is surprising and unexpected because serotonin re-uptake blockers, such as fluoxetine have been found useful and are currently approved only for treatment of an affective disorder, depression. Fluoxetine has also been found useful for treatment of alcohol abuse obsessive compulsive disorder and obesity, but it is not yet approved for use in the United States for these additional indications.

Fluoxetine was found to reduce stress, worry, rejection sensitivity and anger, while increasing mental and physical energy. Additionally, the class of serotonin reuptake blocking agents including fluoxetine is found to facilitate the psychotherapeutic process across a wide variety of diagnoses and symptoms.

The effectiveness of the serotonin re-uptake blockers for each of the above-noted indications and symptoms was found from clinical trial in a private practice of psychiatry. In each instance, fluoxetine was used as the serotonin re-uptake blocker because of its availability and Food and Drug Administration approval in the United States.

BORDERLINE PERSONALITY DISORDER

Fluoxetine was evaluated for borderline personality disorder. Twelve patients with borderline personality disorder and not suffering a major depression were treated with fluoxetine in an open-label trial. All the patients improved. Daily adult dosage ranged from 5 mg to 40 mg. The treatment was generally well-tolerated, but careful dosage titration was important in some patients, especially to manage agitation. The patient ages range from 19 to 54 years old with a mean of 34.7 years old. There were 9 women and 3 men. All of the patients met the criteria for BPD as defined in the Diagnostic and Statistical Manual for Mental Disorders, 3rd edition, revised (DSM-III-R, American Psychiatry Association, 1987). No patient suffered a major depressive episode. All but one of the patients had been suicidal at some point and two of the patients had a history of psychiatric hospitalization. None of the patients were psychotic, nor did any have schizoid or schizoitypol features.

Most of the patients were in weekly psychotherapy and 8 of the 12 patients had been seen for more than one year, 2 had been in treatment for 1 to 3 months, and 2 were new patients. The trial design was open-label and nonblinded. The following table summarizes the results obtained with the 12 patients.

TABLE 1

| Case | DSM-III-R Axis I | DSM-III-R Axis II | Other Previous Psychiatric Disorders | Final Daily Dosage | Global Clinical Rating[a] | Length of follow-up | Relapse when drug stopped |
|---|---|---|---|---|---|---|---|
| #1 | Dysthymic Alcohol abuse Polysubstance dependence | Borderline Dependent | Major depression Bulimia Alcohol dependence | 40 mg | 1 | 26 Wks | Yes |
| #2 | Dysthymic Hypochondriasis Seasonal[b] | Borderline Paranoid traits | Major depression | 5 mg | 3 | 22 Wks | Yes |
| #3 | None | Borderline | Major depression | 30 mg | 3 | 17 wks | Yes |
| #4 | ADHD[c] Cocaine dependence | Borderline | None | 20 mg | 1 | 16 wks | N/A[d] |
| #5 | Alcohol dependence Seasonal[b] | Borderline Narcissistic Dependent | None | 5 mg | 1 | 12 wks | Yes |
| #6 | Cyclothymic LPDD[e] | Borderline Histrionic Narcissistic | Major depression Psychosis NOS[f] Alcohol dependence | 10 mg | 3 | 10 wks | N/A |
| #7 | None | Borderline Dependent | Psychogenic fugue | 20 mg | 2 | 8 wks | N/A |
| #8 | None | Borderline Dependent | None | 10 mg | 1 | 6 wks | Yes |
| #9 | Dysthymic | Borderline Dependent | None | 10 mg | 2 | 6 wks | N/A |
| #10 | LLPDD[e] | Borderline | Alcohol abuse | 20 mg | 1 | 6 wks | N/A |
| #11 | Seasonal[b] | Borderline | None | 10 mg | 1 | 6 wks | Yes |
| #12 | Dysthymic | Borderline Dependent | Alcohol abuse | 20 mg | 2 | 5 wks | N/A | a - Global Clinical Rating 1 - Very much improved, 2 - Much improved, 3 - Moderately improved; b - Subsyndromal Seasonal Pattern Depression, c - Attention Deficit Hyperactivity Disorder (ADHD), d - Not Applicable (N/A), has not discontinued medication; e - Late Luteal Phase Dysphoria Disorder (LLPDD), f - Not Otherwise Specified (NOS)

The assessment of the patients with BPD was made with a 7-point global rating scale based upon physician assessment. The scale ranged from 1—very much improved, to 7—very much worse, with 4 being no change.

PERSONALITY DISORDERS

Thirty-one of the 34 patients with various personality disorders improved significantly on fluoxetine. The treatment appears to exert a nonspecific effect on certain symptoms such as anger, worry, tolerance of stress and rejection sensitivity, regardless of the particular personality disorder. These symptoms are key elements of the personality disorders in general.

Patients with a primary diagnosis of borderline personality disorder often have other personality disorders. See Table 1 for examples.

Ms. A was diagnosed as having Histrionic Personality Disorder. Histrionic Personality Disorder is characterized by a pervasive pattern of excessive emotionality and attention seeking. Ms. A had difficulty asserting herself in a relationship with an alcoholic man and had strained relationships with her grown children and coworkers. After beginning fluoxetine at 10-20 mg per day, Ms. A felt more confident and stronger dealing with others and her ability to relate to people greatly improved.

Mr. B has Narcissistic Personality Disorder, characterized by a pervasive pattern of grandiosity (in fantasy or behavior), hypersensitivity to the evaluation of others and a lack of empathy. He constantly was concerned with what others would think of him. He believed for this reason that he had to have the "perfect woman", because she would be a reflection on him, and was therefore unmarried at age 36. Within several months of beginning fluoxetine at 20 mg to 40 mg per day, the patient relaxed these concerns and married his long-time girlfriend.

PSYCHOACTIVE SUBSTANCE USE

Fluoxetine has been used to reduce craving for alcohol. Medications to assist people to stop using drugs have been very specific to a particular drug. Antibuse and lithium for alcohol, desipramine for cocaine, Clonidine for cigarettes and Methadone for heroin. The present inventive method has surprisingly found that patients may be assisted in stopping various illicit drugs including opiates, benzodiazepines, marijuana, and cocaine. However, fluoxetine was of no help for reducing craving for cigarettes.

Ms. A, Ms. B and Mr. C all expressed a desire to quit cigarettes but experienced no decrease in craving with fluoxetine at doses from 5 mg to 40 mg daily and were unable to quit.

Mr. D noted a decrease in marijuana use which he had been using on an often daily basis after starting fluoxetine at 2 mg to 5 mg per day. He stopped using marijuana completely for one month and had to discontinue fluoxetine because of decreased libido. His craving for marijuana returned after seven days of discontinuing use of fluoxetine and he had two episodes of marijuana usage during the following week. He has since restarted fluoxetine at 1 mg to 2 mg daily and again noticed elimination of his craving for marijuana and no repeat usage.

Ms. E would abuse intravenous and oral opiates, alcohol and benzodiazepines whenever she was upset. This problem existed for many years. Ms. E's use of the drugs completely ceased since beginning 40 mg daily of fluoxetine.

Ms. F had developed a very expensive cocaine habit which she was able to stop with great difficulty during her pregnancy. She had a relapse of usage at the time of beginning treatment with the inventor. She struggled with the craving until she began fluoxetine, and over the next six weeks the craving was lost. The patient had rhinoplastic surgery to repair damage to her nose and to make a symbolic gesture of permanently giving up cocaine use. Unfortunately, Ms. F discontinued fluoxetine due to its cost, and in seven days resumed cocaine use.

Ms. G has been abusing marijuana on a mostly daily basis for many years. Within one month of beginning fluoxetine (20 mg to 40 mg daily), she completely quit and has had no craving for it over a three month follow-up period.

LLPDD

Several cases of LLPDD were substantially improved with fluoxetine. Ms. A had suffered severe incapacitating symptoms of LLPDD beginning about two weeks before her period. She had been seen by the inventor for over one year and had been tried on a number of medications including desipramine, alaprozolam, vitamin B6, and mefenamic acid with very limited success. For example, the desipramine stopped her depressive symptoms (including crying spells) but did not help much in terms of irritability or general ability to function. She has taken fluoxetine for three months at 10 mg to 40 mg daily and has dramatically improved. She reports that she feels and functions better than she has in the past ten years.

Ms. B had been in treatment with the inventor for over two years and suffered severe premenstrual symptoms, primarily irritability which caused the patient and her family great distress. She has been tried on alaprazolam, mefenamic acid, vitamin B6 and buspirone with limited success. The patient recorded marked relief beginning with the first cycle after starting fluoxetine. The relief has continued each of several months since she has taken 20 mg of fluoxetine every three days. She noted return of monthly symptoms if she waited four days between doses.

Ms. C, D, E and F also reported reduction in premenstrual symptoms after beginning fluoxetine in doses of 5 mg to 40 mg daily. These symptoms likewise, had been consistently present for many years in the week before their menstrual period.

The data in Table 1 and herein demonstrate the useful of a serotonin re-uptake blocker for various personality disorders, LLPDD and psychoactive substance use disorders, including cocaine, marijuana, alcohol, narcotics and benzodiazepines.

CIRCADIAN RHYTHM DISORDERS

Ms. A, in her mid-sixties, travelled to Europe with her husband from the west coast of the U.S., a nine- to ten-hour time change. She was taking 20 mg daily of fluoxetine. Her husband suffered his usual symptoms of jet lag, but Ms. A found that she adjusted within a day, which was a first for her.

Ms. B began a new job and had to rise at 3:00 a.m. Early awakening had always been virtually impossible for her and she was pessimistic about her chances of doing it. She found that taking fluoxetine during the morning was stimulating. She was surprised she made the adjustment quite easily.

Ms. C and Ms. D had indications of a phase delay of their circadian rhythms in relation to their sleep-wake schedule. They all found that after beginning fluoxetine, their rhythms synchronized. Both had particular improvement in early morning functioning, where previously they had been half asleep.

Mr. E, while taking fluoxetine for anxiety, remarked that he was going to bed and rising one- to two-hours earlier and felt that his "body clock" had been advanced. He also, like the patients Ms. A, Ms. B, Ms. C and Ms. D in Circadian Rhythm Disorders, had previously, poor early-morning functioning which was greatly improved. Mr. A also evidenced delayed phase of his circadian rhythms which was responsive within one day after beginning 5 mg daily of fluoxetine. The second week he underwent a sleep deprived EEG and slept much of the second day then reported feeling fine. He reported that normally he would be dysfunctional for many days after sleep deprivation and this was a dramatic change for him.

SEXUAL DISORDERS

Fluoxetine has also been found to be useful for sexual disorders. I have found five cases of delayed orgasm, indicating that the use of a serotonin re-uptake blocking agent, such as fluoxetine, is useful in the pharmacotherapeutic treatment of premature ejaculation, a condition currently without effective pharmacotherapy. A pharmacotherapy for premature ejaculation is an important advance because many individuals are reluctant or unable to engage in "sex therapy" with a psychotherapist, or lack for a cooperative partner for assisting with behavioral treatment.

Mr. J was severely troubled by a drive to act out sexually in terms of pornography and masturbation in ways which were morally unacceptable to him and which were causing him difficulties with his wife. Despite his desire to stop, he was unable to do so until beginning fluoxetine therapy in doses of 40 mg to 80 mg daily. He changed from a life-long pattern of needing multiple orgasms per day to being able to go for weeks without sex. He was able to perform well sexually and enjoy sex when he did have relations.

Mr. K was greatly disturbed by perverse sexual desires which he did not act on but were so strong that he had to severely limit his vocational activities to avoid certain situations. He was also bothered by sexual practices he engaged in which were morally unacceptable to him. After taking fluoxetine at 20 mg to 30 mg daily, he happily reported a sharp drop in libido and had no more deviant sexual desires.

Mr. L was uncomfortable with what he viewed as a pattern of promiscuous casual sex. After beginning 20 mg of fluoxetine, he noted decreased libido. After adjusting his dosage down to 5 mg to 7 mg daily, he found that he had no trouble with desire or functioning in his primary relationship, but he had little desire for other casual encounters.

Mr. M had problems with intermittent impotency. This was made worse with fluoxetine which led him to discontinue the medication on several occasions, leading to restored sexual functioning but deterioration in other areas.

Ms. E, F, G and I all noted increased time to reach orgasm when taking 20 mg, 40 mg, 60 mg and 60 mg of fluoxetine daily, respectively. Ms. noted a return of sexual functions when the dose was lowered to 10 mg daily and later was able to tolerate 20 mg. Ms. F, G and I were satisfied with their sexual responsiveness and generally felt sexual relations were improved with the medication. Ms. G commented that she was more patient, "less desperate for an orgasm".

Mr. N was taking 5 mg fluoxetine daily and commented that he had no problems with potency but noted that it took him longer to reach orgasm, and occasionally he was not able to do so. This led Mr. N to discontinue use of fluoxetine with return of regular sexual functioning. He was able to restart the medication at 2 mg daily without again developing this problem.

In summary, 4 of 9 patients, or 44% of the patients using 60 mg or more of fluoxetine per day, reported decreased libido. Currently the only drugs available to suppress libido are quite toxic and used only in cases of dangerous sexual offenders (e.g. rape and child molestation).

SCHIZOPHRENIA

I have made a finding of efficacy with a serotonin re-uptake blocking agent in a woman with chronic schizophrenia. The patient had a limited response to an antipsychotic (Molindone) in high chronic dose of 70 mg to 90 mg per day for two years. At times, the treatment was supplemented with anxiety medications, such as Buspirone or Lorazapam, but these medications also had limited effect. The patient's functioning remained poor in terms of socializing and work, and there was no improvement with higher doses of her earlier medications. Moreover, deterioration occurred every time the Molindone dose was lowered below 70 mg per day. Fluoxetine at 20 mg per day was added to her Molindone at 87.5 mg per day and the patient improved within one week. She completely tapered off the antipsychotic Molindone, over the next three months with no increase in symptoms. The patient has been taking fluoxetine for six months (to date) and her functioning has greatly improved. She has made friends and has joined an amateur musical band. She appears ready to find employment. She had a brief relapse when decreasing the dose of fluoxetine from 20 mg daily to 10 mg daily, but this resolved when the 20 mg dosage was reinstituted.

The potentially devastating long term side effects of antipsychotic drugs currently available (including sometimes irreversible movement disorders, such as tartive dyskinesia and potentially fatal neuroleptic malignant syndrome) make alternatives to antipsychotic drugs a critical need. This patient was able to substitute fluoxetine for her antipsychotic and actually was much improved.

PSYCHIATRIC SYMPTOMS

Fluoxetine was administered to 65 human subjects, only 9 of whom were suffering a major depressive disorder. The results indicate responses across various symptoms and diagnoses, several of which can be applied to a single patient. For example, a patient may have a personality disorder, a drug addiction, and be troubled by symptoms of anger and low energy. One patient was unable to tolerate the initial dosage of 20 mg daily of fluoxetine and dropped out of treatment to enroll in alcohol inpatient treatment. All other patients remained in treatment and were available for follow-up. Several common symptoms were noted to be responsive to serotonin re-uptake blocker therapy. These symptoms included stress, anger, excessive worry, rejection sensitivity and low mental and physical energy.

STRESS

In a group of patients with stress-related symptoms, clear improvement in the tolerance of stress, subjective distress and the ability to function in the face of stress was evidenced by 39 patients. Only one patient with complaints of "stress" was not clearly helped and he has not yet been tried in doses above 20 mg per day of fluoxetine. Nine patients reported improvement in chronic gastrointestinal disorders, which apparently were stress-related.

Two patients experienced palpations of the heart in stress situations and noted that this stopped with the use of fluoxetine. One of the patients, Mr. A. noted that in an emergency situation he usually would feel a brief arrythmia. This resolved with fluoxetine doses of 5 mg to 40 mg per day.

Ms. B, who had always been limited in her ability to function under stress, was able to cope with taking on the "work of three people" during the Christmas season in a floral shop due to the illness of others. Ms. B was able to take on this increased work load while simultaneously having to deal with the news of her father's terminal illness. She remarked she "handled everything better than she ever could have imagined."

ANGER

Anger or irritability decreased in response to fluoxetine treatment. Anger was among the most noted symptom in this patient group and it responded well to serotonin re-uptake blocker therapy. Anger was observed in 37 cases. In only one case where anger was a problem was there not a clear improvement with fluoxetine.

In 9 cases, patients observed improvements in their relationships with their children because they had ceased getting so angry with them. Several remarked that they used to always be yelling at their children and they stopped doing this almost completely. But far from being placid, they were more effectively able to discipline their children and be assertive with adults.

Mr. A remarked that he was hit by another car while driving and normally would have been mad for days, and taken it out on his wife. He remarked he was amazed how well he had taken the whole accident and his family was very impressed with the change.

Ms. C had been in treatment for more than one year and made little progress. After beginning fluoxetine at 10 mg daily, her mother reported that it was "like a switch was flipped." She was no longer angry and irritable all of the time and was able to get along with family members.

REJECTION SENSITIVITY

The beneficial effects of serotonin re-uptake blocker treatment for the symptom of rejection sensitivity was noted. For example, the effect of fluoxetine was observed in 23 patients and improvement was noted within the first week of treatment. Ms. A, diagnosed with BPD (known for prominent rejection sensitivity), had a social gathering for her psychotherapy group. Most members were unable to attend and the group leader reported that instead of this spoiling the evening for her, she enjoyed the company of those who attended and did not even mention the matter in later group sessions. This indicates marked improvement.

Ms. B was unable to ask people to socialize with her because of fear of rejection. After using fluoxetine at doses of 20 mg to 40 mg daily she was able to establish many friendships and extended invitations to her boss, who previously tended to be rejecting.

Ms. C was unable to discipline her children because she feared the loss of their love if she told them "no". After using fluoxetine 40 mg daily, she found her parenting easier and enjoyable.

Ms. D was routinely devastated by being called into her supervisor's office. Minor criticism would disturb her for many days thereafter. Since beginning fluoxetine at 20 mg every 3 days, she is not bothered by occasional critical remarks and continues to be doing an excellent job.

Mr. E had always been exquisitely sensitive to rejection. Upon beginning fluoxetine, at approximately 10 mg per day, within one week he was no longer living in "fear of rejection." He had to stop the medication for a period of time because of decreased libido and within a week of cutting back he again regained his rejection sensitivity. An example was kicking an adult student out of class for reading during his lecture. The problem again was resolved with restarting fluoxetine.

WORRY

Worry is another symptom that was found responsive to serotonin re-uptake blocking therapy. Six patients were found to be suffering from the symptom of excessive worry and the symptom was independent of any depressive episodes.

A specific type of worry is a hypochondriasis. This is recognized disorder defined in DSM-III-R. Hypochondriasis is a preoccupation with the fear of having, or the belief that one has, a serious disease based on the person's interpretation of physical signs or sensations as evidence of physical illness. The unwarranted fear or belief of having a disease persists despite medical reassurance. It is not of delusional intensity. The person can acknowledge the possibility that he or she may be exaggerating the extent of the feared disease or that there may be no disease at all. The individual's preoccupation may be with bodily functions, such as heartbeat, sweating, or peristalsis, or with minor physical abnormalities, such as a small sore or an occasional cough. The individual interprets these sensations or signs as evidence of a serious disease. The feared disease or diseases, may involve several body systems, at different times or simultaneously. Alternatively, there may be preoccupation with a specific organ or a single disease as in "cardiac neurosis," in which the person fears or believes that he or she has heart disease.

Mr. A constantly worried about his health (hypochondriasis). He was always seeking medical examinations to reassure himself that he did not have a fatal disease. Upon being given fluoxetine at 5 mg to 20 mg daily, he largely dropped his health concerns from therapy sessions and no longer sought unnecessary medical examinations.

Mr. B also suffered from hypochondriasis accompanied by nonspecific abdominal complaints, which severely limited his daily functioning and contributed to his not working for several years. His worry and abdominal complaints largely resolved upon a fluoxetine dosage of 60 mg daily and he was able to return to work.

Mr. C was a self-employed small businessman who had done very well financially for more than 20 years, but constantly worried about money matters. After beginning fluoxetine at 4 mg per day, he was finally able to stop worrying and enjoy his financial success.

Mr. D constantly worried about critical moments he faced in his occupation. Every time the phone rang he would worry that he would be called in to deal with a critical situation that he would not be able to handle. After beginning fluoxetine at 5 mg per day, he is now able to greatly reduce worry and he can, at times, enjoy his work.

Ms. E constantly worried about her children, especially about the possibility of their drowning. Within a week after beginning fluoxetine at 20 mg per day she noted a decrease in her worrying. She reported a striking example of being able to take a nap while her children were with a friend on a boat. She stated that previously, she would have worried constantly until their return.

Ms. F also worried excessively about the safety of her children, to the point that she was embarrassing her thirteen year old boy by her overprotectiveness. Within five days of taking fluoxetine at 20 mg per day she noticed a dramatic decrease in worry and was able to adopt a more relaxed attitude with her son.

MENTAL OR PHYSICAL ENERGY

The energizing affect of serotonin re-uptake blocking agents such as fluoxetine, has been found to be fairly gentle, and possibly more related to correcting circadian rhythm disturbances or reducing stress than to actual stimulation. For example, Ms. A was not suffering a depressive disorder but reported she always had been completely exhausted at the end of her work day and unable to socialize or otherwise function effectively in the evenings. Upon beginning fluoxetine at 20 mg every 3 days she had a better level of energy throughout the day and had no awareness of any stimulant feeling.

Ms. B was non-depressed and reported she cut her coffee consumption down by at least 50% in the weeks following beginning fluoxetine at a dose of 5 mg to 20 mg per day. She had "needed" and used 15 to 20 cups of coffee per day.

Mr. C was not depressed but has multiple sclerosis and found he fatigued easily mentally and physically. Upon beginning fluoxetine at a dose of 1 mg to 2 mg per day, he had more energy to get through his work day. Mr. C experienced dramatic improvement in mental energy, which was especially reflected in his ability to concentrate well enough to enjoy reading once again.

Ms. D was not depressed but had become extremely sedentary. Upon beginning fluoxetine at 20 mg per day, she felt "much more energetic" and began exercising.

Ms. E, a non-depressed patient, reported that she never had energy to do any housework after each day and had to leave everything for the weekend. Since beginning fluoxetine at 7 mg to 20 mg per day, she finds she is able to function well in the evenings and do a little each day and have her weekends free.

Mr. F was not depressed, but was always so exhausted by the end of the day that he could never volunteer for overtime. Since beginning fluoxetine at 20 mg per day he has much more energy and he has been able to work overtime whenever needed.

FACILITATOR OF PSYCHOTHERAPY

Serotonin re-uptake blockers have been shown to enhance or facilitate psychotherapy. Facilitation of psychotherapy was observed in 21 cases when it was possible to make a before and after comparison. The majority of these patients had been in therapy with the inventor for over nine months prior to receiving serotonin re-uptake blocker therapy. Their baseline functioning in psychotherapy was well established and their changes were readily apparent. In no cases was there apparent interference with psychotherapy, although in many cases, the patients decided that they no longer needed psychotherapy because of their improvement. For example, Mr. T was superficial and rambling in his session. Whenever he confronted an emotionally charged issue, he would start to ramble as an apparent attempt to escape from a stressful area. It was impossible to have a true conversation with Mr. T, as the patient would not, on his volition, stop to allow a reply or a question. That went on for months. In the first session after beginning fluoxetine, the patient dramatically relaxed his defensive posture and allowed an interchange. This occurred despite no change in his symptoms or mood in the first seven days of taking fluoxetine, as noted by the patient. Over the next few weeks the patient was able to let go of his preoccupation with a particular worry and make progress in a number of areas.

Further examples are Mr. M and Mrs. D, both had difficulty working with the principles of standard cognitive therapy because their rejection sensitivity was so severe that they could not believe it was possible to handle situations as discussed in their reading assignments. After fluoxetine treatment, they were not only able to learn these principles but to apply them in real-life situations.

Mr. G and Mr. M had sexual issues that they had not been able to talk about. After beginning fluoxetine, the patients were not overwhelmed by these stressful issues and hence were able to address them.

Ms. H was in weekly therapy for over a year and had been unable to acknowledge her motivation for infanticide, while totally denying any awareness of the act and, at times, the pregnancy itself. In the weeks following treatment with fluoxetine, the patient was finally able to confront this issue. It appeared that her decreased sensitivity rejection allowed her, to reveal things about herself which formerly she suppressed.

Mr. D's main problem in therapy was a tendency to intellectualize and deny his feelings. He was in psychodynamically oriented therapy for nearly one year before beginning fluoxetine, though he previously had been given medications for anxiety and depression. At the time of fluoxetine administration, he was not suffering a depressive disorder, or even experiencing depressed mood, but he responded dramatically in a number of aspects. In psychotherapy, he was more able to identify and express his feelings, perhaps because they were less threatening (i.e., decreased anger).

Mr. E had been seen for over a year by the inventor and previously, by a psychologist. He had received medication for anxiety, but this was of slight help. He made little progress in his therapy, in part, because of his preoccupation and worries about his health (hypochondriasis). Upon beginning fluoxetine this issue largely dropped from sessions. Although, not depressed at this time, he, nevertheless, lacked mental energy or motivation for change. After beginning fluoxetine, he made substantial progress.

The following examples illustrate case vignettes of patients' results from administration of fluoxetine. The examples are intended to illustrate the benefits of a serotonin re-uptake blocker administration in a series of patients whose psychiatric disorders and symptoms are noted. The examples are not to be construed to limit the indications for serotonin reuptake blockers to the specific symptoms of the patients illustrated, nor to limit the invention to the specific serotonin re-uptake blocker used.

EXAMPLE 1

Ms. A (Case #1 in Table 1) is a 38-year-old married woman with one son and a primary diagnosis of borderline personality disorder. She was hospitalized at age 14 following a suicide attempt made in response to a parental conflict. A similar attempt occurred at age 20. She had recurrent conflicts with neighbors, coworkers and her husband. She stated "At times, I just go crazy—throwing knives and everything." Ms. A had extreme rejection sensitivity and would often become suicidal or abuse alcohol or drugs in response to conflict. A major crises of some type occurred almost weekly. She had a poor self-image and felt that her identity within the family was obscured by her sister's prominent role. She complained of frequent boredom, and her mood was labile with prominent states of anger, depression and anxiety.

The patient was bulimic from ages 14 to 30 and was alcohol dependent from roughly age 32 to 36. She suffered a single major depressive episode around age 32 which lasted a year and a half and was only partially responsive to doxepin. This drug was given at probably inadequate dosage because of poor tolerance. Ms. A had been seen in the inventor's practice for 14 months prior to beginning fluoxetine, in generally weekly cognitive-oriented psychotherapy. A trial of buspirone decreased anxiety, but made the patient more depressed. Benzodiazepines (including alprazolam) were helpful in managing periods of high stress. No other antidepressants were utilized prior to fluoxetine.

The trial of fluoxetine was initiated at 20 mg every morning. Ms. A reported feeling generally worse on days 4 through 10, with difficulty sleeping, headache and a feeling of extreme "vulnerability." However, all of this did not make her feel depressed, which surprised her. On her own volition, she then doubled her dosage and switched to taking the medication at bedtime. She noted dramatic clinical improvement over the next several days with good tolerance of the medication. Within one month of taking fluoxetine, the patient terminated psychotherapy by mutual agreement, and continued to receive fluoxetine (40 mg daily) from her health maintenance organization. Follow-up interviews of the patient, at 5 and 6 months after initiating the trial, revealed the effect had been sustained continually over the interval.

She returned to school and reported handling this well in addition to working full-time. She has not abused alcohol or illicit drugs, and has stopped taking benzodiazepines. She spontaneously, reported missed doses for several consecutive days, and a brief return of symptoms within the week. She stated that since the beginning of the trial, "I feel 100% better. I actually like Mom and Dad now, I'm well-liked at work, I don't ruminate on the negatives, I don't have murderous rages, my marriage is five times better." There was no evidence of hypomania; this level of enthusiasm was representative and essentially defining of a global clinical rating of 1 (very much improved).

EXAMPLE 2

Mr. B (Case #2 in Table 1) is a 20-year-old man living with his parents. His primary diagnosis is borderline personality disorder. His functioning since his mid-teens has been characterized by: unstable intense relationships; impulsivity with respect to alcohol use and reckless driving; affective instability with prominent anxiety, irritability, and depression; intense anger with frequent talk of wanting to kill the objects of his anger; recurrent physical fights with his younger brother; several periods of suicidal threats; persistent identity disturbance manifested in self-image and fluctuating career goals (e.g., spy, race car driver, etc.); and chronic feelings of boredom. There were prominent paranoid personality traits, but no psychotic symptoms. He had co-existent dysthymic disorder and hypochondriasis.

At the time of presentation over one year prior to the study, the patient was in partial remission from a major depressive episode. He did not meet criteria for seasonal pattern of depression but appeared to have fall/winter exacerbations of symptoms. The patient had been in treatment with the inventor for 15 months prior to the fluoxetine trial and had demonstrated limited response to buspirone, alprazolam and several benzodiazepines. He had always refused standard anti-depressants because of fear of side effects. He began fluoxetine at 20 mg per day and within about five days noted a clear change in mood. He felt almost no anxiety or depression and most strikingly, little anger. This was evident on an almost daily basis, because other drivers would regularly infuriate him.

He noted he was less inclined to worry about his health, and largely dropped this topic in sessions. Mr. B initiated a reduction in session frequency from weekly to every other week. He stopped his medication for a period of several days and noted a return of symptoms which abated with reinstatement of medication. Three months after starting fluoxetine, he developed a problem with what he described vaguely as a spasm in his chest which would occur occasionally. His symptoms also began to recur about this time, and it is unclear whether this represented a fading of the effect of fluoxetine or noncompliance. The patient's family asserted, contrary to the patient, that he stopped taking his medication when he believed he was suffering side effects. He has recently agreed to take 5 mg of fluoxetine per day and his family confirms he is once again showing significant improvement in terms of brighter mood, less anger, improved school performance and increased sociability. This patient was rated the least improved of the patients in this series, (i.e., 12 patients in Table 1), and is representative of a global clinical rating of 3 (moderate improvement).

I claim:

1. A method for enhancing the treatment of a disorder selected from the group consisting of circadian rhythm disorder, borderline personality disorder, hypochondriasis, late luteal phase dysphoric disorder, psychoactive substance use disorder, sexual disorder and schizophrenia comprising, administering a therapeutically effective, nontoxic dose of fluoxetine, and derivatives and pharmaceutically acceptable salts thereof.

2. The method of claim 1 wherein the serotonin reuptake blocker is fluoxetine or norfluoxetine.

3. The method of claim 2 wherein the daily adult dose of fluoxetine or norfluoxetine is from about 2 mg to about 80 mg.

* * * * *